United States Patent [19]

Paoluccio et al.

[11] Patent Number: 4,965,887
[45] Date of Patent: Oct. 30, 1990

[54] FACE PROTECTOR FOR SPLASH AND SPATTER PROTECTION

[75] Inventors: John A. Paoluccio, P.O. Box J, 5038 Salida Blvd., Salida, Calif. 95829; Dennis R. Hoover, Modesto, Calif.

[73] Assignee: John A. Paoluccio, Salida, Calif.; a part interest

[21] Appl. No.: 249,595

[22] Filed: Sep. 26, 1988

Related U.S. Application Data

[63] Continuation-in-part of Ser. No. 119,696, Nov. 12, 1987, abandoned.

[51] Int. Cl.$^5$ .................................................. A61F 9/04
[52] U.S. Cl. .......................................... 2/9; 2/13; 2/205; 128/863; 128/201.25; 351/158
[58] Field of Search ................... 2/9, 202, 205, 206, 2/13, 427, 10, DIG. 7; 128/857, 858, 201.12, 206.19, 201.25, 863; 351/158

[56] References Cited

U.S. PATENT DOCUMENTS

| | | | |
|---|---|---|---|
| 1,199,529 | 9/1916 | Collman | 128/863 |
| 2,579,942 | 12/1951 | MacLean | 128/201.25 |
| 2,724,834 | 11/1955 | Henderson | 2/13 |
| 3,089,145 | 5/1963 | Kiefer | 2/13 X |
| 3,183,523 | 5/1965 | Harrison | 2/13 |
| 3,458,866 | 8/1969 | De Man | 2/13 X |
| 3,991,753 | 11/1976 | Viesca | 2/9 X |
| 4,589,408 | 5/1986 | Singer | 128/857 |
| 4,671,775 | 6/1987 | Hill | 2/202 X |
| 4,701,965 | 10/1987 | Landis | 2/9 X |
| 4,805,639 | 2/1989 | Dial et al. | 2/9 X |
| 4,821,340 | 4/1989 | Johnson | 2/9 |

FOREIGN PATENT DOCUMENTS

| | | | |
|---|---|---|---|
| 0074877 | 3/1929 | Sweden | 128/863 |
| 0556664 | 12/1974 | Switzerland | 128/863 |

*Primary Examiner*—Peter Nerbun
*Attorney, Agent, or Firm*—Robert S. Smith

[57] ABSTRACT

A device for protecting the face including the eyes, nose, ears or mouth, which includes a rectangular shaped plastic member, first and second clips fixed to the rectangular shaped member, the first and second clips being disposed for engagement with associated eye glasses worn by the user of the device. In one form there is fixed to the top and sides of the rectangular shaped member a multiple layered fabric used as a head cover. The outer layer is fluid absorbent, the middle layer is fluid impermeable, the inside layer that touches the skin of the wearer is fluid absorbent. In one form of the invention a support frame is further included that comprises an elongated brow member, temple members having a curved section for engaging the ears of the user and respective hinge members joining the temple members and the elongated brow member, the clips are disposed on the rectangular shaped member for engagement with the temple members.

6 Claims, 11 Drawing Sheets

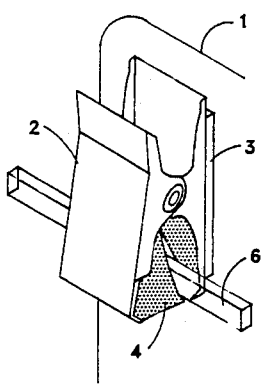
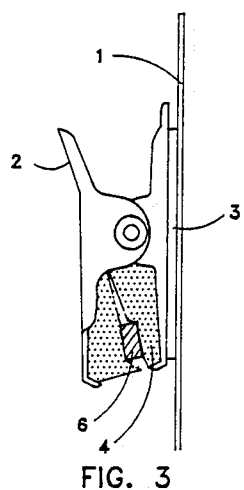
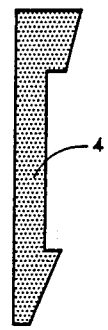
FIG. 2               FIG. 3               FIG. 3A
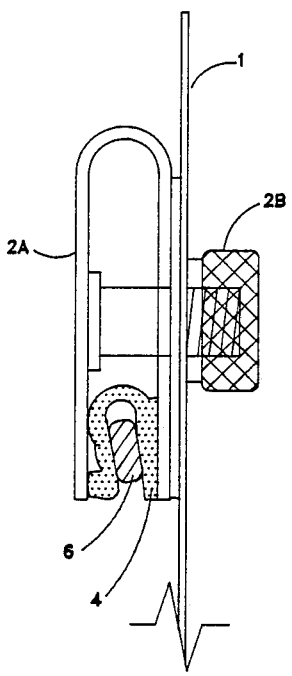
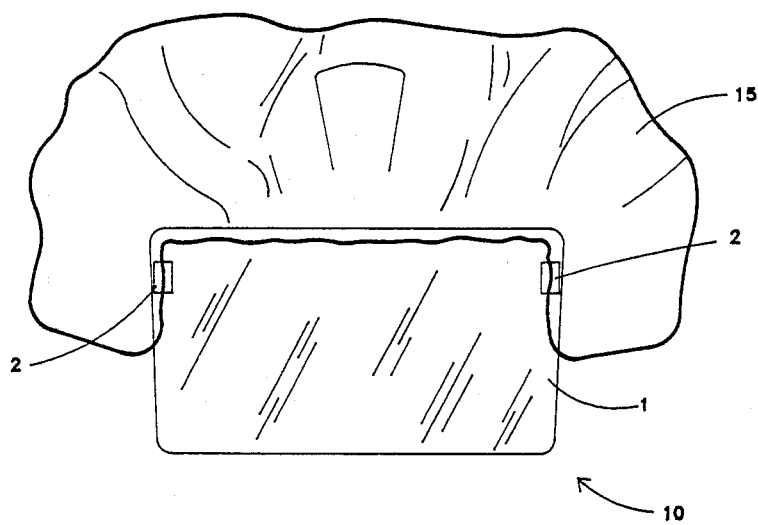
FIG. 4               FIG. 5

FACE PROTECTOR FOR SPLASH AND SPATTER PROTECTION

RELATED APPLICATIONS

This application is a continuation in part of U.S. patent application Ser. No. 119,696 filed Nov. 12, 1987 now abandoned.

BACKGROUND OF THE INVENTION

The invention relates to safety devices and particularly to face shields for use in medical fields and the like. Large heavy duty shields have been and are being used in many construction fields. These shields like welding helmets, abrasive shields and related items like safety goggles, safety eye glasses and masks have generally protected the eyes from flying particles. Filter masks have protected the wearer from breathing dust and chemicals.

The prior art includes the following U.S. Pat. Nos:. 3,991,753; 1,199,529; 2,446,048; 3,183,523; 2,724,834; 3,089,145; 3,458,866; 4,076,373; 4,701,965. The prior art also includes Swedish patent document 74877 and Swiss patent document 556664.

Specifically in the medical field, safety eye glasses and more recently surgical masks and head covers are being used for protecting the mucous membranes of the eyes, nose and mouth. This is partly due to contagious diseases such as AIDS, hepatitis and herpes. These devices have proved to be very unsatisfactory for protecting the wearer and they are very uncomfortable to wear for long periods. Face shields, safety eye glasses and surgical masks and head caps that protect the wearer from spatter, such as experienced in medical fields including dentistry have led to a variety of improvements to older head-mounted shields. Although, lighter and not as bulky, they still have numerous deficiencies including:

1. They fog up the eyeglass lenses of the user.
2. They mess up the wearer's hair.
3. They put pressure on the wearer's head.
4. They are uncomfortable to wear for prolonged periods.
5. They interfere with the user's movement.
6. Some known units will slip on the head of the user and create uncomfortable pressure areas on the wearer's.
7. Many shields do not accommodate a wide variation in user head size and shape and hair style size and shape and thus are not particularly suitable for women professionals.
8. Certain surgical masks have proved to be very ineffective when they become moist because bacteria and viruses migrate through the masks through osmosis or siphon means.
9. Many safety eye glasses do not protect wearer from spatter at the sides and bottom of the eye glasses.
10. They often are very obtrusive and thus may be unacceptable, to the patient. In some cases, a patient undergoing minor care may feel he is undergoing major surgery when they see a doctor with eye glasses and a surgical mask.
11. Surgical masks interfere with speech and visual communications including facial expression which a patient relies on to remain relaxed.
12. The cost of the present protection methods substantially increase the cost to medical patients.
13. Head caps do not fit over the various eye protectors to form a protective seal.
14. Head caps do not allow for ventilation out the top, therefore, cause heat and moisture to build up.
15. During certain medical procedures, large quantities of blood can spurt on the head cover and flow over the face shield.
16. Due to the discomfort of the existing methods, many choose not to wear protective face shields and risk infection.
17. Safety goggles that have extensive side protection close to the wearer's skin reduce ventilation at the eyes. Proper ventilation is most important for removing heat and moisture, and for preventing perspiration from getting into the eyes. The hot, humid air conditions also encourage bacterial growth and is detrimental to the eyes of the wearer, especially if the wearer wears contact lens.

At present it is cumbersome or very expensive to provide face protection from fluid spatter. Several devices including goggles, surgical mask and head caps are worn to protect the wearer. Frequently these items do not match or accommodate the different size and needs of the wearer.

The net result is improper protection. It is common for significant fluid splash to land on a doctors head cap and run down his face or shield. With the many separate combinations of face protection components now worn, fluid can make contact with the doctor's face. Especially if the doctor is perspiring, even a small portion of contaminated fluid can have disastrous effects.

The present invention has particular application to the medical field. Those skilled in the art will recognize many other applications and uses when used with safety eye glasses. These include:

1. Medical doctors, nurses, and hospital staff
2. Dentists and technicians
3. Hospitals, nursing homes, and the like
4. Pharmacists
5. Laboratories
6. Electronics
7. Light industry
8. Painters
9. Beauticians
10. Visitor's at hospitals
11. Visitor's at factories
12. Personal protection when mowing lawns
13. Mechanics
14. Protects workers in food processing plants from wash down spray.
15. Protection against agricultural and other sprays
16. Protection against small flying particles.

An object of the invention is to provide an effective, simple to use, low cost, comfortable and practical combination spatter shield, support and head cap that protect the wearer and encourages it's use. Contagious diseases such as AIDS, herpes and hepatitis are changing the habits and procedures of practicing medical and other health care and medical personnel. The need for a medical face protector shield such as the present invention answers a current and future need. Many hospitals and health care facilities have gone to disposable bedding, liners and other supplies. A disposable low cost medical face protector such as the present invention is in line with the current trend. However, the shield does lend itself to washing and re-use when desired, and the head cover can be replaced.

An object of one embodiment is to provide a complete apparatus for those who do not wear eye glasses or for conditions where safety eye glasses are not necessary to protect the user from heavy projectiles.

It is a further object to enable the user to simply install glassless frames, which become the structural support for the two clips of the shield.

An object is thus to offer spatter protection without the unnecessary additional glass lenses that are normally worn.

One major object of the invention is to provide overall face protection against fluid spatters with one combination unit.

A further object of this invention is to provide eye and face protection in these numerous fields of work where workers put their eyesight in jeopardy because a practical, lightweight, comfortable device did not exist and the wearer relied on only open sided safety eye glasses. One major overall object is to reduce the number of unnecessary eye injuries, some of which result in blindness as well as to prevent infection by shielding the exposed mucous membranes of the eyes, nose, mouth and ears from contagious diseases.

SUMMARY OF THE INVENTION

It has now been found that these and other objects of the invention may be attained in a device for protecting the face, including the eyes, nose ears or mouth, which includes a rectangular shaped plastic member and first and second clips fixed to the rectangular shaped member. The first and second clips are disposed for engagement with associated eye glasses worn by the user of the device. A multi-layered head cap is integrally attached to the top and sides of the shield. This cap has an integral plastic fluid impermeable layer with a fluid absorbent outer and inner layer. The outer layer absorbs fluid spatter and prevents its migration. An extra thick layer is positioned at the forehead area to capture excessive retained fluid splash in the special trap or formed near the connections to the shield. The inside absorbent layer comes in contact with the wearer's skin and hair and acts to absorb perspiration and to provide a comfortable contact surface. The top of the cap has a special formed ventilation opening to keep the wearers face cool and for preventing the shield from fogging up. In another form of the invention a support frame is provided that includes an elongated brow member, temple members having a curved section for engaging the ears of the user and respective hinge members joining the temple members and the elongated brow member. The clips are positioned on the rectangular shaped member for engagement with the respective temple members. The clips may be spring loaded and may be disposed proximate to the edges of the rectangular shaped member. The clips may be lined with an elastic material which may be rubber. The rectangular shaped member may have a curvilinear edge. The clips may be disposed proximate to edges that are on opposite sides of the rectangular shaped member.

BRIEF DESCRIPTION OF THE DRAWING

The invention will be better understood by reference to the accompanying drawings in which:

FIG. 2 is an enlarged view of the spring loaded clip secured to the temple frame of the wearers eye glasses.

FIG. 3 is an enlarged cross section view of the clip. This shows the rubber lining deformed around the temple frame. FIG. 3A is an enlarged view of the molded rubber liner before insertion into the clip to act as the liner.

FIG. 4 is an enlarged cross section view of an alternate clip that allows for screw adjustment outside of the shield in lieu of a spring loaded clip.

FIG. 5 is a view showing the invention in the flat unused position.

DESCRIPTION OF THE PREFERRED EMBODIMENT

Figure 1:
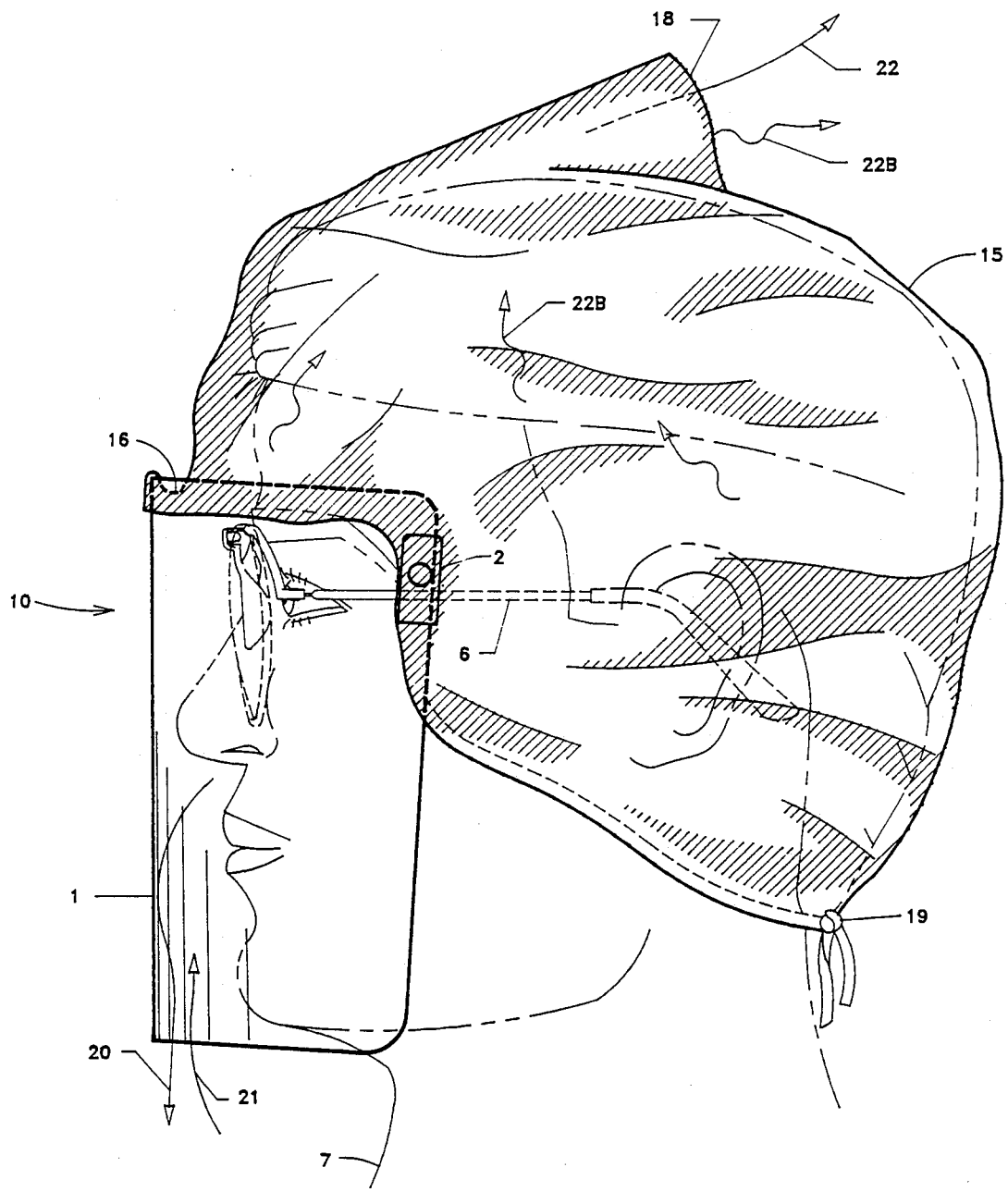
FIG. 1 is a schematic view of the device in accordance with one form of the invention. The view shows the head cover fastened to the polycarbonate shield. It also shows the ventilation opening on top. Clips are shown fastened to the wearers glasses. Clips may be of screw type adjustment as show in FIG. 4. This allows external adjustment with a small knob outside of the shield.
Figure 6:
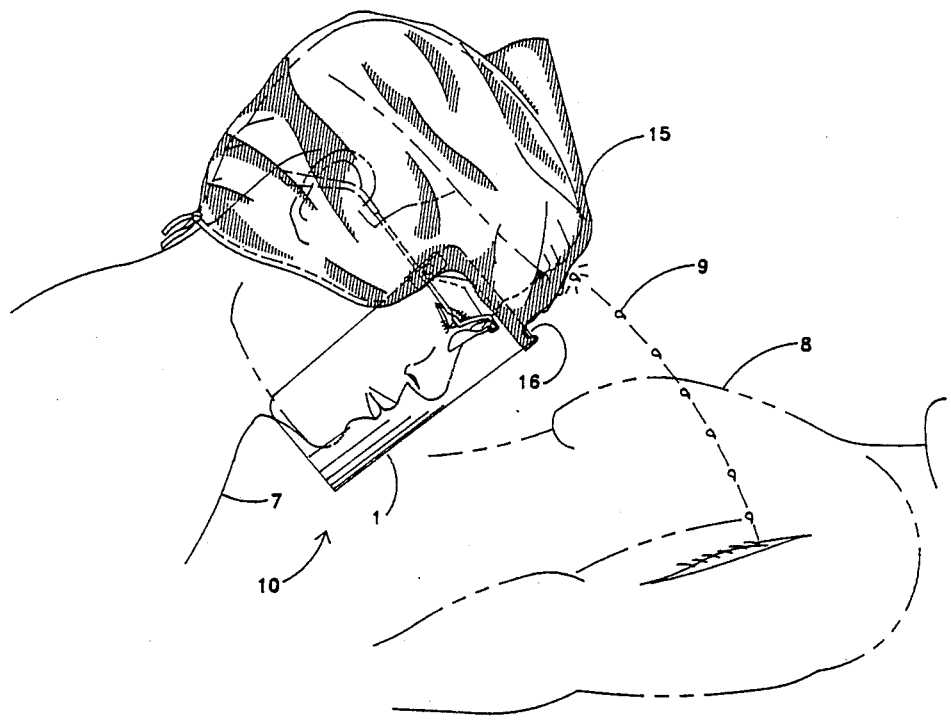
FIG. 6 is a side view of the invention in use. A doctor is shown being spattered with blood from the injury of a patient.
Figure 7:
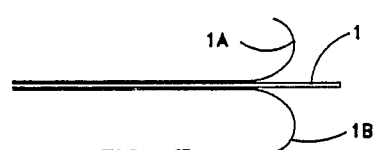
FIG. 7 is a partial cross section of the shield material with the release liner on each side partially removed.
Figure 8:
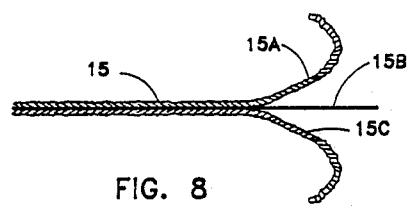
FIG. 8 is a partial cross section of the head cap material showing the various layers in a peeled back view.
Figure 9:
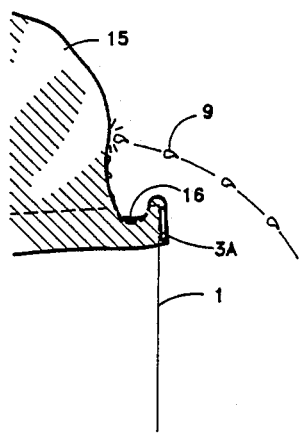
FIG. 9 is a partial view of the offset in the head cap where fluid splatter is retained.
Figure 10:
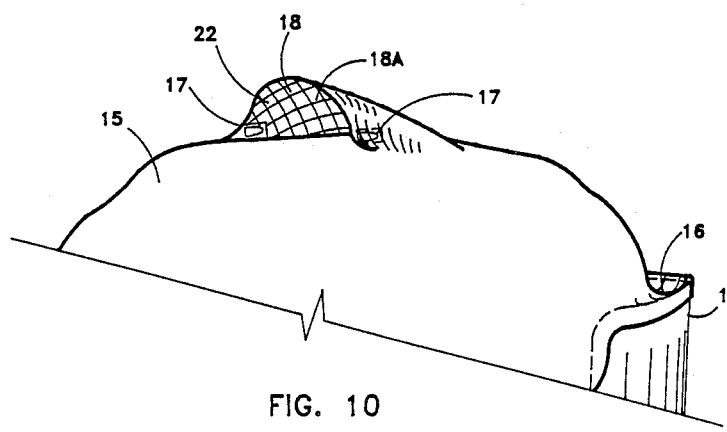
FIG. 10 is a schematic view of the vent opening at the top of the head cover.

Referring now to FIGS. 1-22, a medical face protector 10 is shown attached to the wearer's 7 eye glasses 6. A clear lens shield 1 material is shaped to offer maximum protection for a wearer 7 against fluid splatter 9 generated while working on a patient 8. Two spring loaded clips 2 clamp on the temple frames of the eye glasses 6. A rubber lining 4 is disposed around the frame 6 between the jaws of the clips 2. The curvature of the shield 1 is formed when the clips 2 are attached to the frames 6 of the eye glasses and forms an arc shaped, structurally sound arrangement. The back side of the clip 2 is fastened to the shield 1 with double-coated, pressure sensitive, high-tack adhesive tape 3. A head cover 15 which is secured to the top and sides of shield 1 is shown draped over the wearer's 7 head.

Figure 11A:
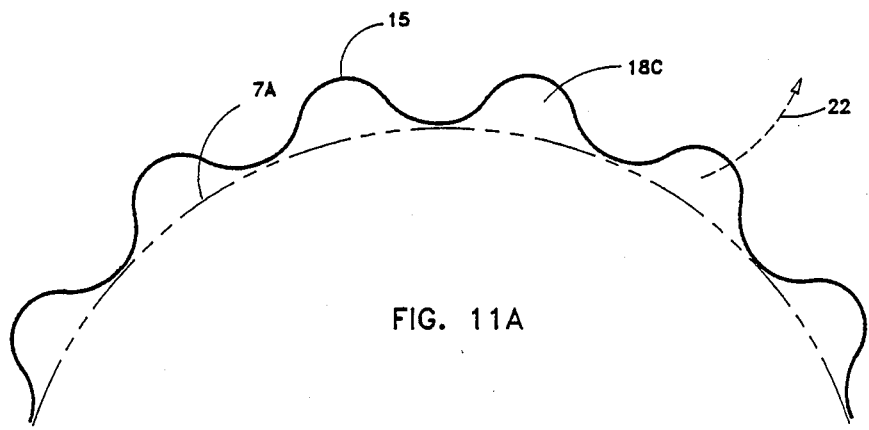
FIG. 11A shows the fluted top in cross section.
Figure 11:
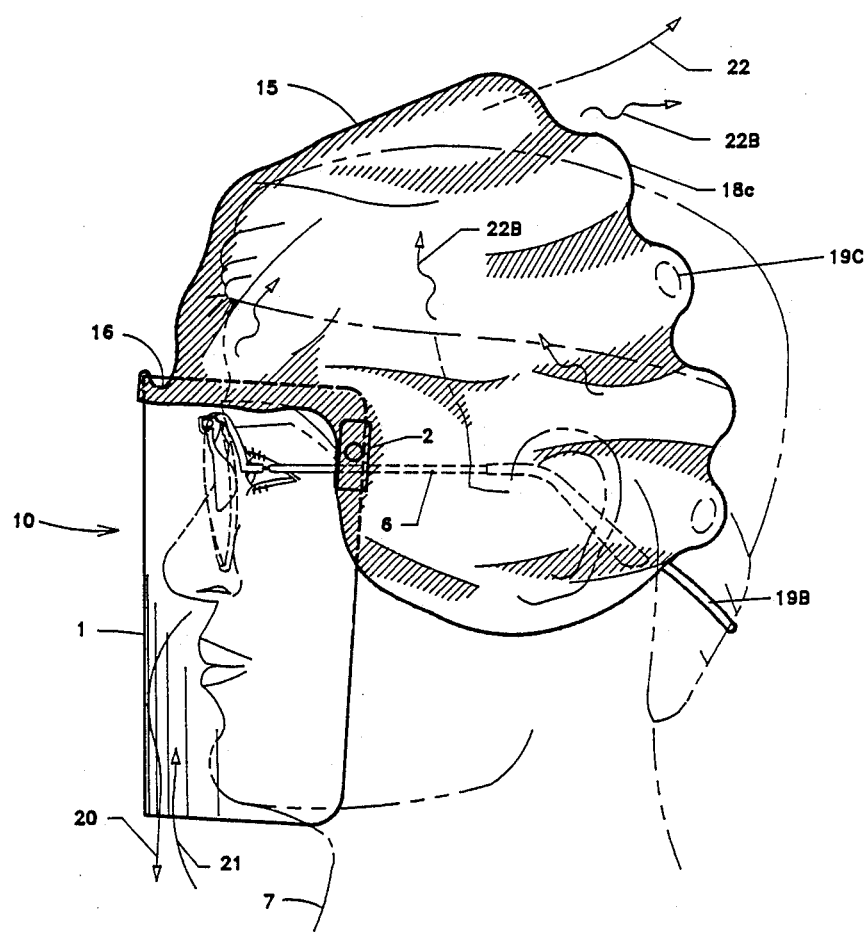
FIG. 11 is a schematic view of the device in an alternate form at the invention. This mini-cap is shown with a fluted top to aid in ventilation.
Figure 15:
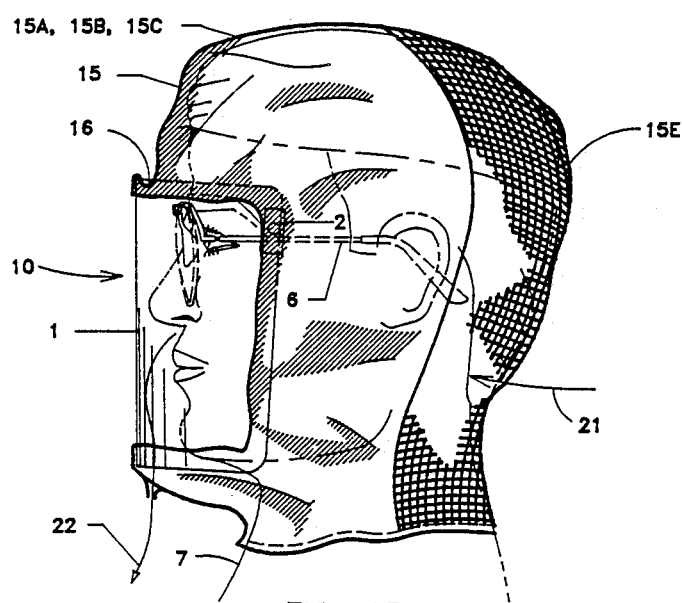
FIG. 15 is a schematic view of another form of the invention showing the head cover with a single layered rear section. In this view the large rear portion is made of a high efficient filtering material to allow breathing air to be filtered free of air borne bacteria. An exhaust air relief flipper back draft damper is also shown at the chin area.

The partial head cap is fabricated from the 3 ply material as shown in FIG. 4. The head cover 15 has draw bands 19 that are used for adjusting its fit. The head cover 15 is attached to the shield 1 with double stick tape 3A. This tape 3A can be a low tack material pre-fastened to the head cover 15 so that it is possible to only change the head cover 15 should it be soiled. However the entire low cost assembly 10 can be used as a one piece disposable medical face protection, where in high tack tape 3A would be used. The head cover 15 can have excess absorbent material 15A in the forehead area 16 where it attaches to the shield 1. This is where the head cover 15 material folds down and rises back up to from a fluid retention trap 16 near the forehead of the wearer 7. This head cover 15 is made of multiple layer material. The outside layer 15A is fluid absorbent which acts to capture and retain fluid spatter. The center layer 15B is an impermeable light weight plastic liner that prevents fluid or bacterial transfer through the cover. The inside layer 15C is an absorbent layer that acts to absorb perspiration from the wearer 7 and to provide a comfortable contact surface where it contacts the face surface, namely the forehead area. The head cover 15 has a raised ventilation opening 18 which is located above the wearers 7 head. This ventilation opening 18 acts to exhaust the warmed humid air generated by the wearer 7. The exhaled air 20 is virtually totally exhausted out of the bottom of the medical face protection each time a breath is exhaled. The high velocity of the exhaled air leaving the nostrils easily travels the smooth unobstructed path at the bottom portion of the shield 1. Heat is generated by the warm surface head temperature, perspiration, and by a portion of the breathing exhaled air 20 of the wearer 7. This lighter, warmed air rises around the surface of the head and exhausts out the raised opening 18 which works on a stack effect principle. The approximately 10" distance between the cool dry room air 21 which enters at the bottom of the medical face protector and the ventilation opening 18, approximately 2 square inches opening area, is sufficient to cause a continual flow of air flowing up over the wearers face thereby keeping moisture buildup and temperature low. Another version of the invention which can be worn is shown in FIG. 11. This version is a simpler less cumbersome version that has certain obvious advantages and disadvantages. It protects less area but is more open and offers frontal and side face protection. The head cover in this version only covers the brow, approximately ⅛ the top of the head, ears and side of the face. The head cover 15 material is preformed into a fluted pattern 15D of semi-circles. this form creates an ideal path for ventilation air to exit the top 18A of the device, thereby keeping the wearer comfortable. Another version of the shield is shown in FIG. 15.

Figure 12:
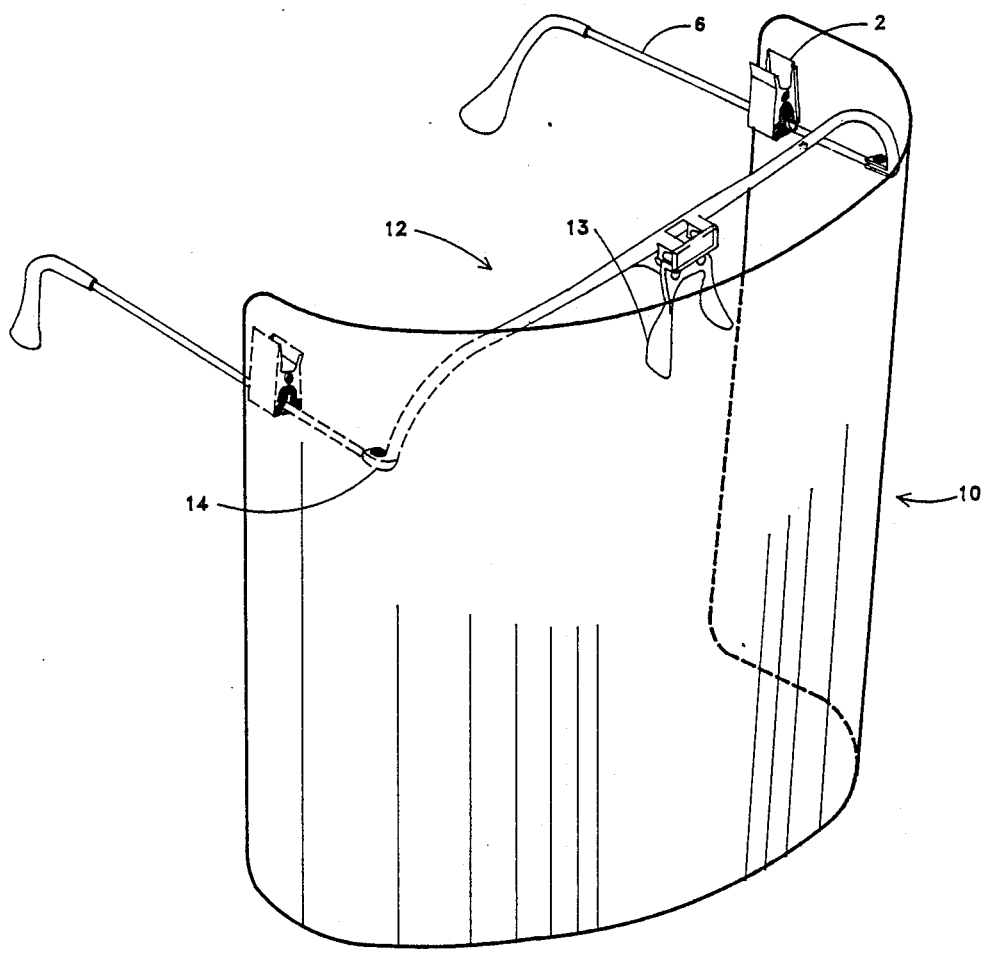
FIG. 12 is a schematic view of the glassless frames with shield but without head cap. The face shield may be used in this fashion.
Figure 14:
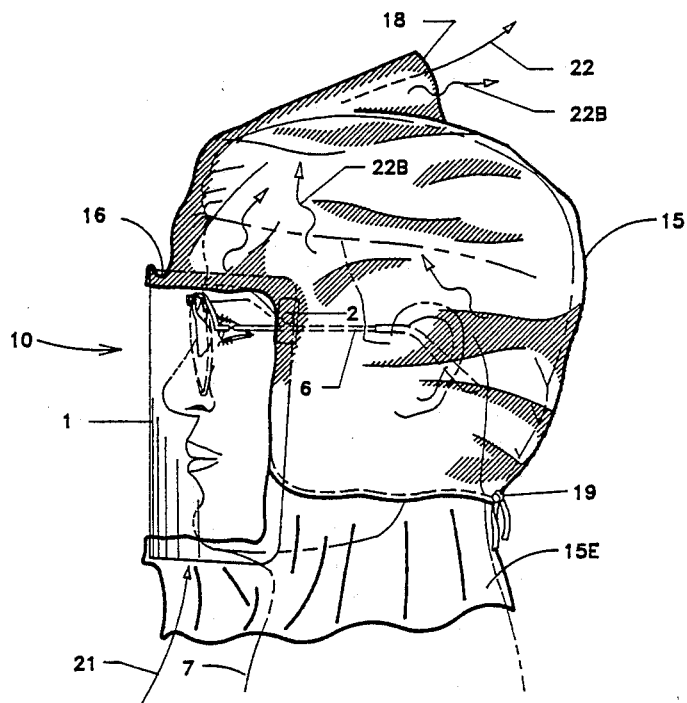
FIG. 14 is a side view of the invention as shown in FIG. 1 with an optional skirt attached.
Figure 16:
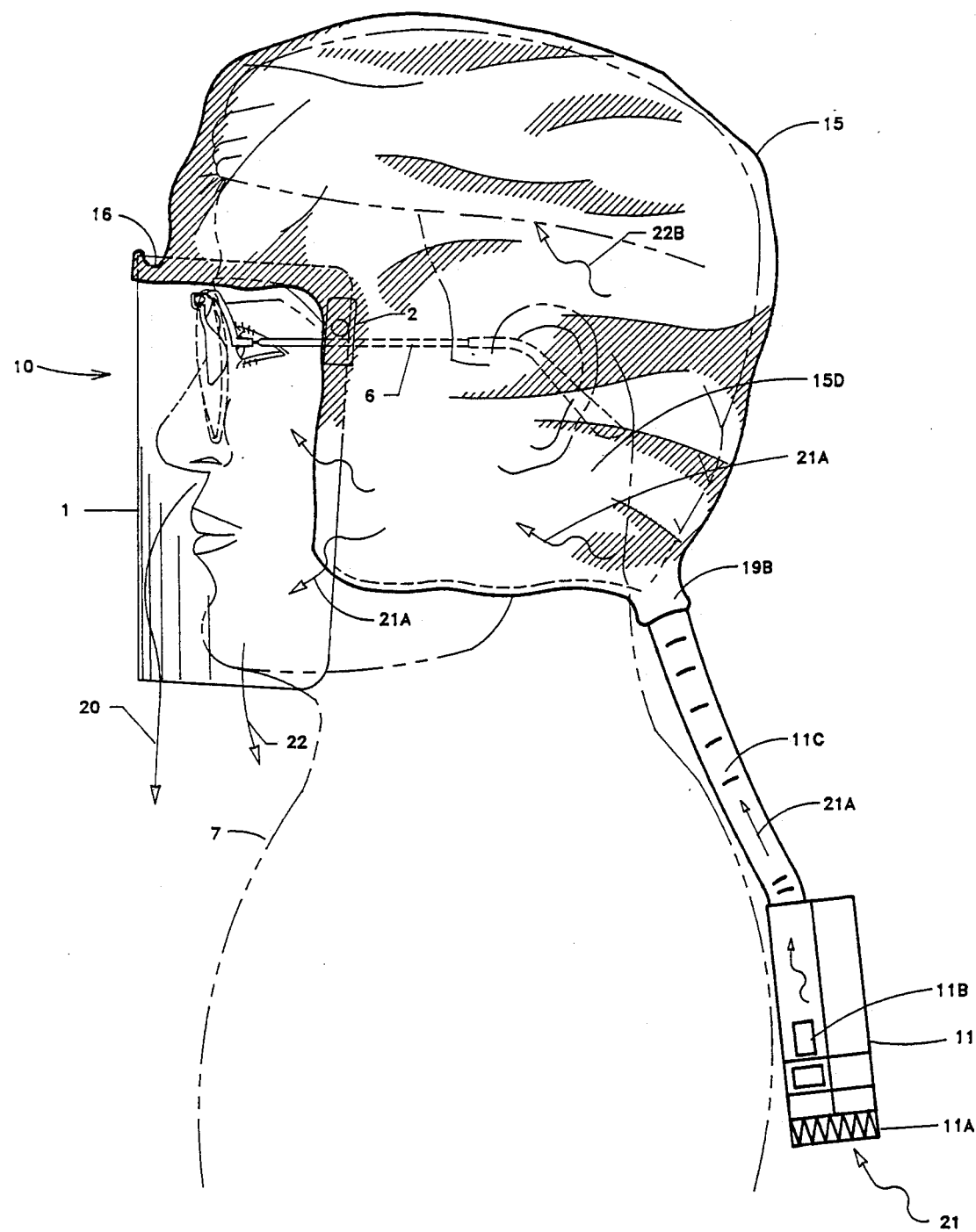
FIG. 16 is a schematic view of another form of the invention shown with a battery powered backpack filtered air supply unit attached to the medical face protector.
Figure 17:
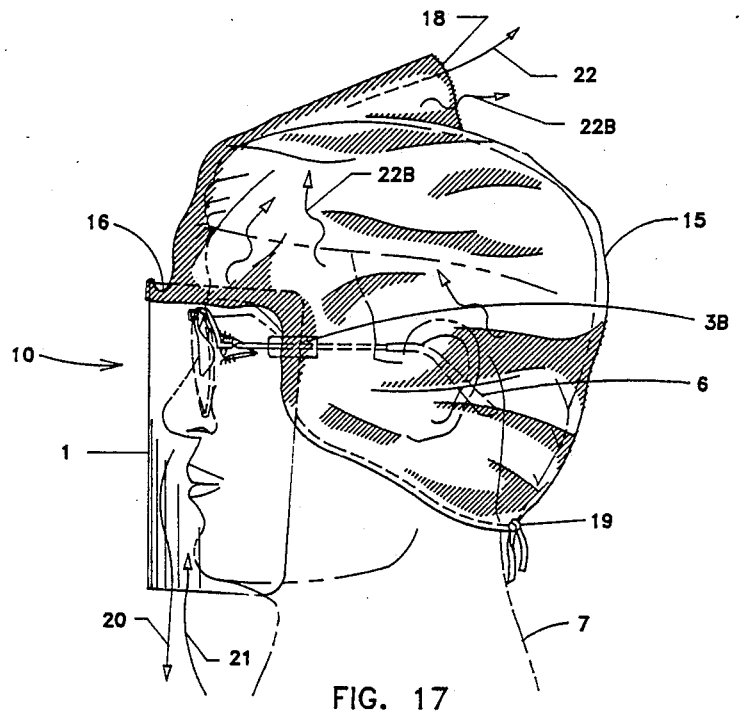
FIG. 17 is a schematic view of another form of the invention with supporting frames secured to the shield with double stick tape in lieu of clips.
Figure 18:
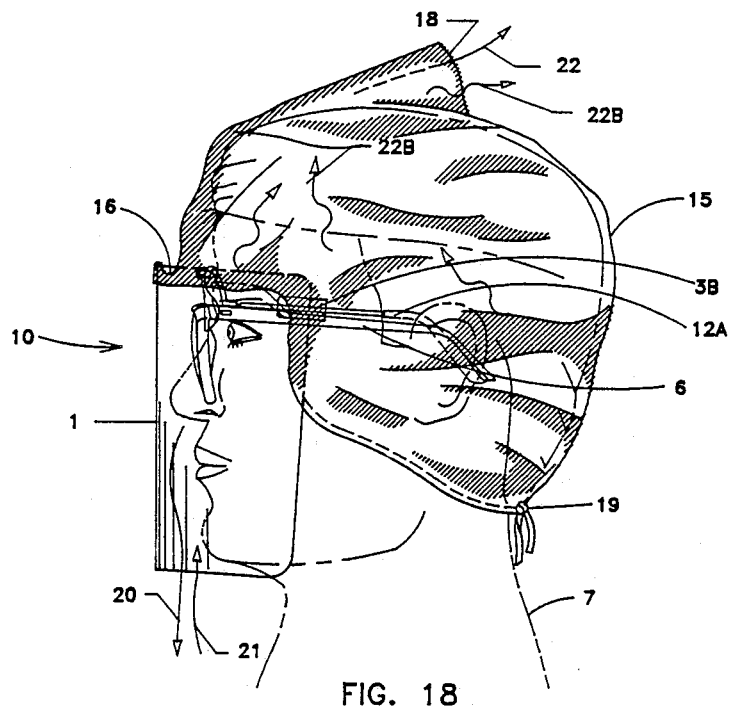
FIG. 18 shows the same unit as in FIG. 17 but with safety glasses also being worn. There is no fastening between the supporting frames and the wearers glasses.
Figure 19:
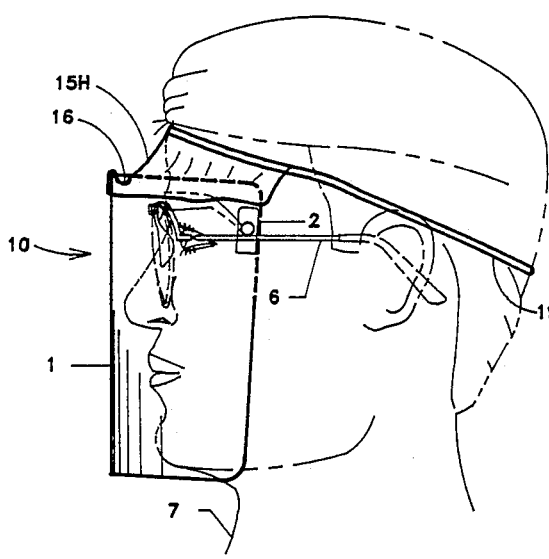
FIG. 19 is a schematic view of another form of the invention with a flexible protective head band that forms a tight seal with a draw band. This is for limited splash protection at the forehead area.
Figure 20:
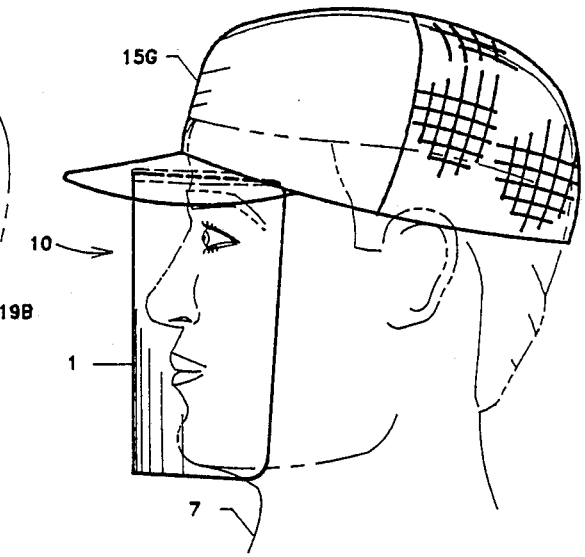
FIG. 20 is a schematic view of another from of the invention where the shield is secured with double stick tape to a baseball cap type head cover. The cap is the supporting structure.
Figure 21:
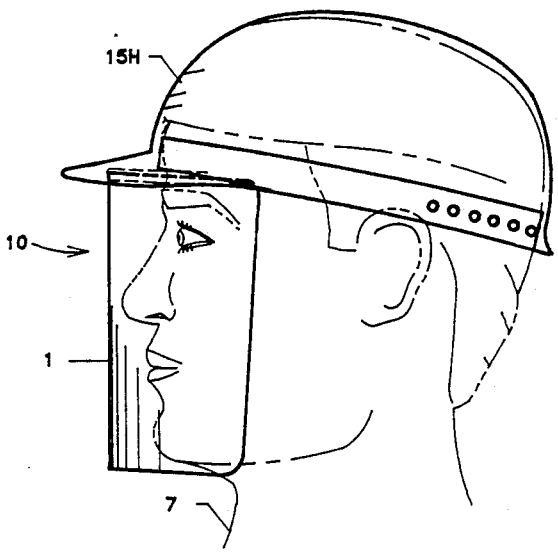
FIG. 21 is a schematic view of another form of the invention where the shield is secured to a workers lightweight bump hat. The shield can be fastened with clips or tape.
Figure 22:
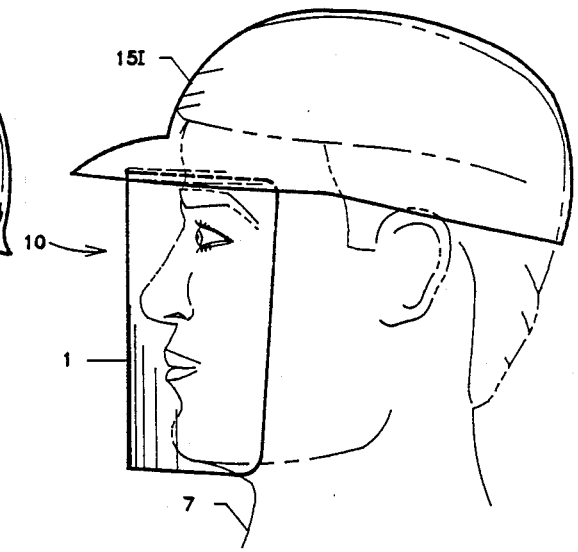
FIG. 22 is a schematic view of another form of the invention where the shield is secured to a clear, lightweight, semi flexible, head cap with a sponge like liner to hold it in place.
Figure 23:
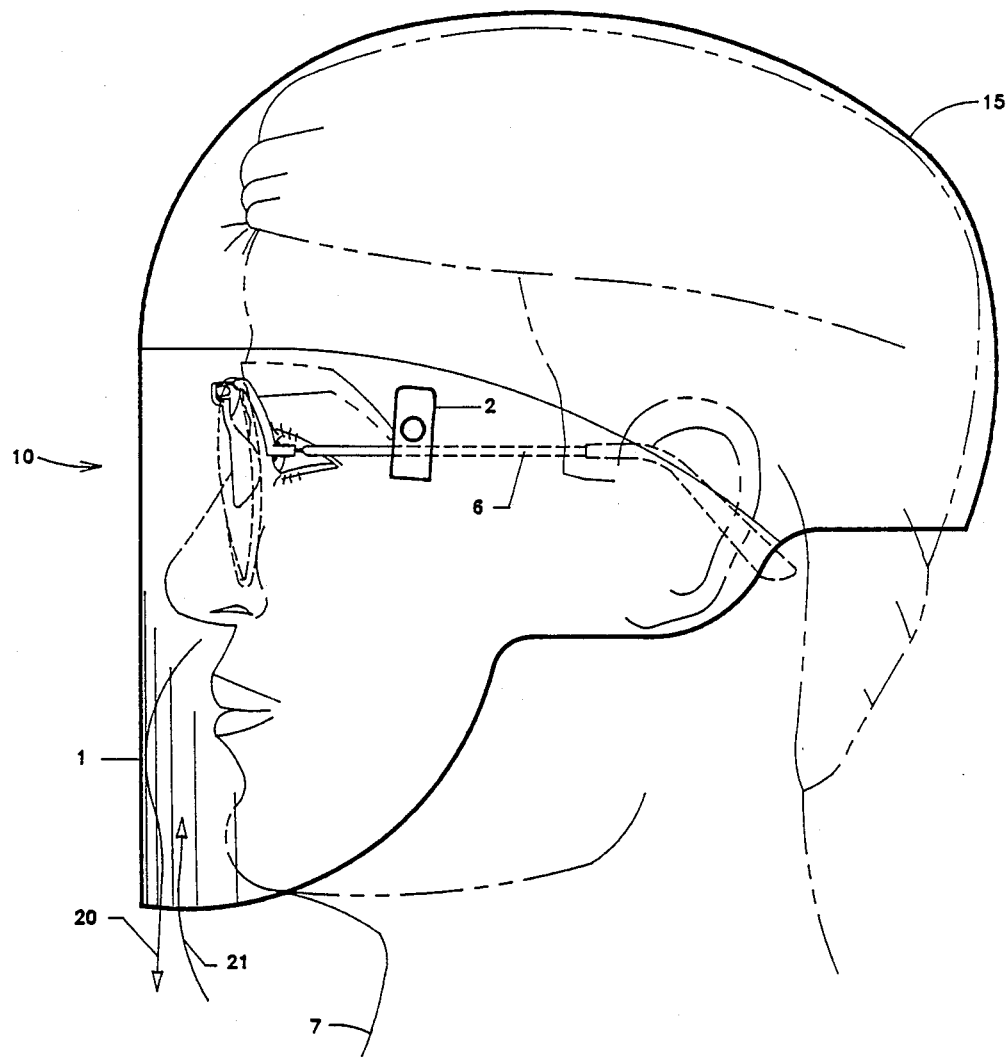
FIG. 23 is a schematic view of another form of the invention where the entire unit is made of one continuous piece of sheet plastic. The top portion is press formed with heat to form the shape of a head cover while the lens portion is left cold. This makes the lens form a semi-circle. The cap is large enough to shield the head but does not need to touch the head. The two clips securely support the entire unit. The unit could also be fabricated in two separate pieces and bonded together.
Figure 24:
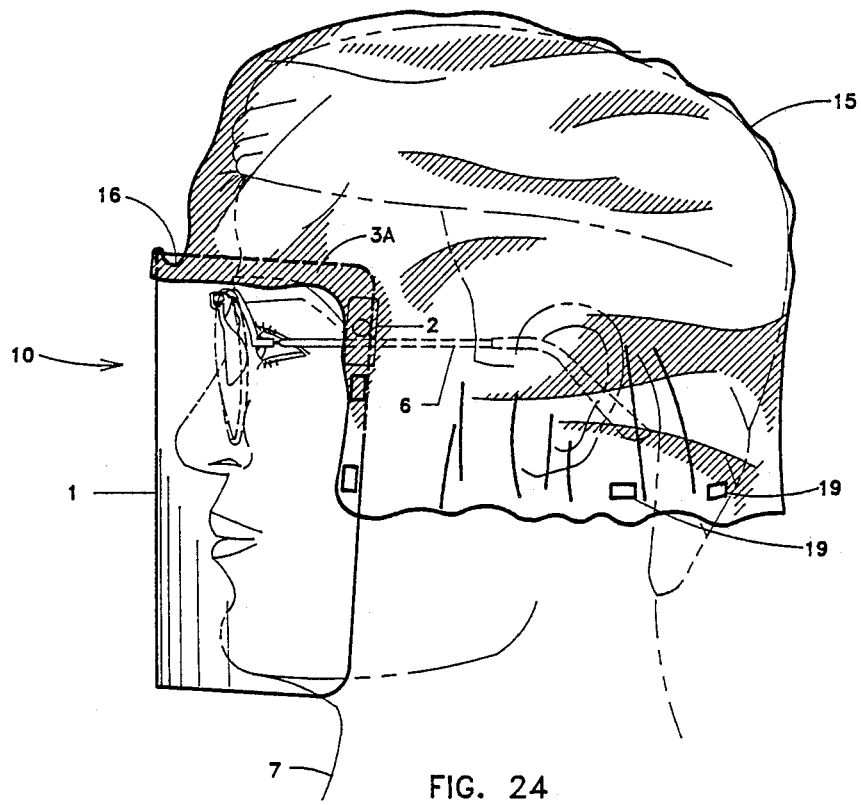
FIG. 24 is a schematic view of another form of the invention that shows a simple draped head cover with low tack tape to hold lightly the head cover in place. In this form the head cover can easily be replaced.
Figure 25:
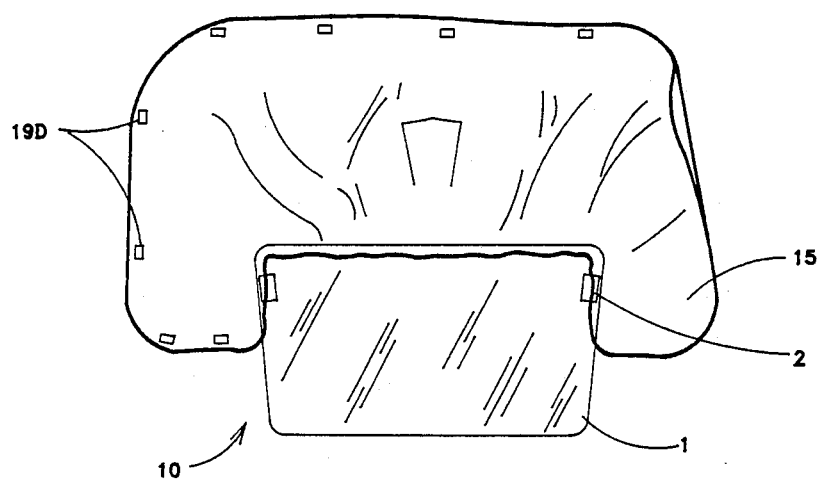
FIG. 25 shows the same unit in FIG. 24 in the flat, laid out position.

This version would be used where protection from breathing aerosol vapors carrying bacteria from the patient is desired. The head cover 15 is draped over the entire head and is secured at the neck area. A vent release flapper valve 22 is located just below the shield 1 and could be extended closer to the nostrils if desired. The force from the high velocity exhaled air 20 forces the fabric flapper valve 22 to open which allows the exhaled air 20 to exit through this opening. Inhaled air enters through the rear portion 15E of the head cover. This portion of the head cover is made of a high efficiency filter fabric such as that found in HEPA filters. These filter down to 0.3 micron with low air pressure drops with low air velocities as are present when inhaling. The shield 10 can be fitted on the glassless frames 12, as shown in FIG. 12, which are an accessory part of the device. Other applications for the device, in accordance with the invention and in addition to the use for protecting against spatter, include a ventilating barrier, wherein a battery operated blower 11 can supply or exhaust air to the mask area as shown in FIG. 16. Other variations include an extension bottom skirt as shown in FIG. 14; adhesive fastened support frames as shown in FIG. 17 and 18; a partial brow protector as shown in FIG. 20; another version where the shield is fitted to a workers bump hat is shown in FIG. 21; and another version where the head cover is a lightweight preformed material such as the shield material or even thinner and more flexible to form a transparent, disposable cover and cap is shown if FIG. 22.

In a preferred form of the invention the apparatus includes:

1. A clear face shield that provides a barrier against direct spatter. The sides of the shield wrap fully around the sides almost to the ears of the wearer. The shield material may be 0.01" thick polycarbonate with protective release liner on each side to protect the optical clear surface from scratches and dirt until ready for use. When ready for use, one simply peels off the release liners and discards them.

2. A head cap that is securely fastened to the top and sides of the face shield with double-faced adhesive tape. The unique properties of this head cap includes multiple layers of materials with features as follows: a. A fluid absorbing outer surface such as absorbent paper with extra absorption material near the forehead area. b. A lightweight fluid impermeable inner layer for at least a portion of the head cover with a texture such as Saran (Trademark) Wrap. c. A fluid absorbing inside surface, for at least a portion thereof, that comes in contact with the wearers hair and skin to absorb perspiration. d. An excess of material is folded and shaped at the forehead area to causes a trap for fluid splash that acts to retain the splashed fluid while it is being absorbed, near the connection point between shield and the head cap. e. An oversized head cover with drawn string(s) or band(s) to accommodate almost any size head or hair style. f. The head cap portion is extremely lightweight so as to cause no discomfort. g. The head cap portion is extremely pliable. h. The head cap is secured, in some embodiments, with low-tack double-stick tape to allow changing caps easily and still maintains a secure seal. High tack tape can be used on disposable models. i. The rear portion of the head cap may be a single absorbent layer that allows air to pass through to facilitate ventilation. j. The top portion of the head cap may be fitted with a raised vent opening that works on the principal of stack effect. As the wearer breathes and as the head gives off heat it warms the surrounding air. This warm air rises and exhausts out the top vent opening. As the warm moist air exits the top, an equal quantity of cool dry room air enters the bottom of the shield. The cool dry air then flows over the face area so that moisture buildup is minimized.

This flow also helps keep the shield from fogging up. The interior of the vent chamber is lined with a fluid absorbent surface to capture any back splash. The opening itself can be filled with hair netting in certain cases. The vent opening may have streamlined or belled exit to increase exhaust air efficiency. This vent opening may be formed with the head cap material by making a cut in the material, raising and taping the bottom portion which causes the top to open up. The vent opening can also have a raised curved portion causing an aspiration effect, that is, as the wearer moves around room air passes around the vent opening which causes a low pressure area that further increases the ventilation effect.

3. There are two clips that are used to attach the shield assembly to the wearers glasses. These are spring loaded clips with rubber lining. The rubber liners have a special shape that causes the bottom portion of the shield to be angled in at the chin area and the sides. The clip liner is contoured to accommodate almost any temple frame from very thin to very thick. These two clips allow for the shield to obtain a structurally sound shape when the shield is bent and formed into an arc and the clips being attached to glasses.

4. Supporting frames are an option which can be provided when safety glasses are not needed. These glassless temple frames with a bridge support are lightweight and transfer the full shield weight to the three support points of the ears and bridge of nose.

5. An optional extended skirt may be attached to the bottom of the shield to provide even further protection. This skirt may be tucked into the shirt of the wearer or extend over the shirt and under a medical coat. k. A variation of the head cap is shown in FIG. 12. This depicts a smaller shield version and covers eyes, nose, mouth and ears but leaves part of the top and all the back open for the maximum in ventilation to protect against heat and moisture buildup.

The advantages of the face shield in accordance with the present invention, which simply clips onto the wearer's eye glasses, and have a head cover include:

1. Provides an impenetrable barrier against fluid spatter, bacteria and viruses which is effective protection for the eyes, nose and mouth, and ears.

2. Protection against excessive fluid splash with resultant drips that are retained and absorbed by top front portion of the head cover.

3. Low enough in cost to be disposable without the need to keep soiled and spattered shields and head cover, and yet the shield portion is durable enough to be reused if the wearer desires. The durability is possible because the shield is manufactured out of durable plastic, such as polycarbonate 0.01" thick. Although washable and tough it is preferable to discard a shield that has been spattered.

4. Sufficiently open on top and bottom to allow for significant ventilation to disperse the wearers exhaled breath and heat to prevent fogging up of the lens, and to cause a continuous flow of cool room air over the wearer's face.

5. Very attractive in appearance with an almost invisible shield.

6. The shield portion does not come in contact with wearer's head, hair, or any other part of the body. The head cover portion simply lays over the hair for full protection.

7. Does not mess the wearer's hair. Being light weight and oversized, it simply lays over any size hair style.

8. Does not interfere with wearer's movement.

9. Easy to install. Clamps tightly to frames of eye glasses and does not slip. Head cover can be tightened with draw bands.

10. Easily adjustable to almost any position.

11. Fits any size head or hair style even if the wearer is using magnifying lenses that are spaced well away from the eye ball of the wearer.

12. The patient does not find the shield to be at all obtrusive. The patients can see all the facial expression of the wearer.

13. Speech and visual communication is totally maintained between the doctor and the patient. When the doctor wants to hide his facial expressions a surgical mask can be used.

14. Low cost and thus the cost of patient care is reduced.

15. Comfortable to wear even for long periods.

16. Simple and quick to install.

17. The attaching clips clamp on the frames of the eye glasses to cause the shield to form a circular arc surrounding the wearer's path of vision.

18. Compactness—when not in use the shield lays flat with head cover folded in a compact manner.

19. The flat nature of the apparatus when not in use makes the device in accordance with the invention easy to ship, transport and store which further reduces their cost.

20. The clips can attach to almost any size eye glass frame.

21. The clips have cushioned rubber lined jaws that tightly clamp onto any eyeglass frames without scratching the finish of the wearer's eye glasses temple frames.

22. The head cover can be in a variety of shapes to give different levels of protection.

23. The medical face protector is very lightweight.

24. The shield may be tinted or fitted with a tinted covering. In some forms the lens may be laminated with material to protect the wearer's eyes from intense ultraviolet light. Tinted safety glasses may also be worn for light protection.

25. Each side of the shield lens is supplied with a thin plastic protective release liner that can easily be removed just before use therefore keeping the lens as clear and clean as possible.

26. The medical face protector keeps the face and eyes well ventilated with maximum air flow without any vision obstruction, while still maintaining maximum fluid spatter protection.

27. The support frame increases the field of vision because there is no lower lens frame or additional lens to look over or through.

Figure 13:
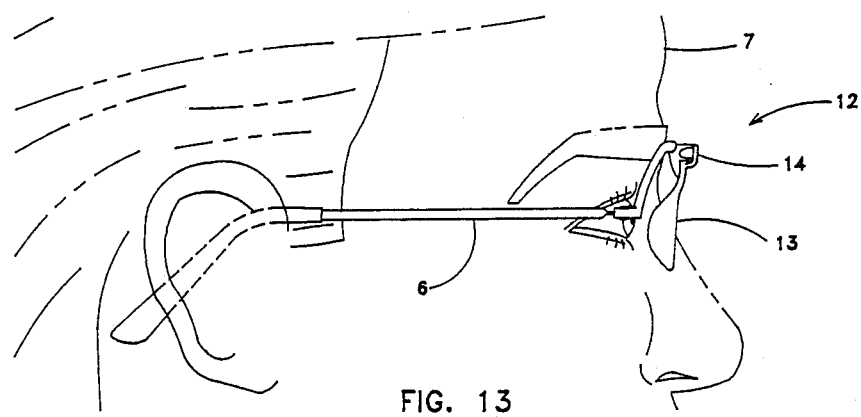
FIG. 13 is a side view of the glassless supporting frames. No shield or head cover are shown for clarity.

FIGS. 12–13 show another embodiment of the invention in which a frame 6 comprising two temples are coupled with respective hinges 14 to an elongated brow member 14 that carries nose pads 13. This embodiment is particularly adapted for users who do not routinely wear eye glasses. This embodiment also includes a lens 1 as in the other illustrated embodiments.

The face protector of the present invention is a simple, low cost, ultra lightweight, clear, and distortion free plastic face shield and head cover. In one form the device attaches directly to the wearers eye glasses. It is disposable and is ideal for doctors, physicians, nurses, medical lab technicians, and other health care auxiliaries to protect the face area, (Specifically the mucous membranes of the eyes, nose, ears and mouth), from blood and saliva spatter and/or splash from these or other substances. The medical face protector in accordance with the present invention can be used in medical, dental and related fields where protection is desired from blood and saliva spatter and splash. The spatter from an infected patient may carry virulent transmittable diseases such as AIDS and hepatitis. These diseases infect doctors and medical health care personnel via the mucous membranes of their eyes, nose, ears and mouth. The shield will provide a total barrier to these susceptible areas. New laws will require that protection devices such as this be used by the medical and dental profession. One variation of the present invention utilizes a support frame that fits over the ears and rests on the nose exactly like conventional eye glasses. In this variation, however, there are no eye glasses or glass holders. There is only the frame surrounding the face from ear to ear with the support pads that rest on the nose. This becomes the support frame for the accompanying face shield.

Ordinarily the lens or shield material is a clear, plastic type material that is tough and lightweight such as polycarbonate. Ordinarily the material is rectangular or precut into a special shape as shown in the drawing. The overall dimensions are approximately 0.01" thick by 10"×6" in the preferred embodiment. The material when laying flat has little structural strength but when formed into an arc and secured rigidly at its ends with clips, forms a sound simple structure.

Affixed to the shield are two spring loaded metal clips. These are secured with high contact double coated pressure sensitive foam tape. This tape is between the shield and the back side of the clip. This permanently bonds the clip to the plastic shield. Other adhesives may be applied instead of the double coated or faced tape. Installed between the jaws of each clip are rubber strips which line the total contact points of the clips. These are form fit and can be fastened with adhesive to the clip to keep them firmly in place. The rubber lined jaws of the clip when opened wide will fit over a large variety of metal or plastic temple frames including thin metal frames or thick plastic frames. The soft cushioning effect of the rubber lining firmly clamps over and depresses around the frames of the eye glasses. This holds the clip fast without slipping or movement while protecting the finish of the temple frames from damage. The rubber lining has a sloped face that causes the lens to be inclined inwardly at the lowermost part of the lens and thus improves the protective characteristics of the shield around the jaw area. The clips are spaced far enough apart so that they fit almost all eye glasses. The adjustable feature of moving the clips back and forth along the frames, while the clips are partially depressed, allow for final adjustment. With a little practice, the wearer is able to install and adjust the clips without ever removing his eye glasses. The head cover can best be adjusted by looking in a mirror and securing the draw bands.

Although the aforementioned shield has been shown and described with respect to medical applications it should be understood that the shield has numerous applications to other fields. One particular version with or without the head cover would be practical for light commercial and industrial such as non-hazardous splash or spray as may be used in painting. Another version would include safely glasses and the shield less head cover for home or at work such as wood working to keeping light sawdust or small low energy particles from hitting the face.

The invention has been described with reference to the illustrated preferred embodiments. Persons skilled in the art of constructing medical face protectors may, upon exposure to the teachings herein, conceive variation in the mechanical development of the components therein. It will be understood that the clips shown in the drawing may be clips utilizing springs or screw adjustments or clips that are merely elastic plastic arms or snap like connectors joining the lens and the support frame. In some forms of the invention a plurality of holes may be provided to accommodate various size requirements. Thus the user may select the hole that is most suitable for the particular use. The support frame may be provided with a knob or protrusion to engage such holes. The head cover including multiple layered fabric, ventilation openings, absorption material, fastening method, filtration media and the like shall apply to numerous variations to suit different applications. The claims shall be construed to mean that the term clip includes such structure. Such variations are deemed to be encompassed by the disclosure, the invention being delimited only by the appended claims.

Having thus described our invention, we claim:

1. A device for protecting the face including the eyes, nose, ears and mouth, which comprises:
   a clear plastic member disposed generally in the form of a cylindrical section;
   two spring loaded, rubber lined clips fixed on said member at spaced points and securing said member proximate to the edges thereof to associated temple frames of associated eyeglass frames, said member being covered with protective release liner on both sides to keep it protected from scratching and dirt until ready for use;
   said member having attached to the top and sides thereof a multiple layered head cover;
   said head cover having a fluid absorbent outside layer for absorbing fluid spatter; a fluid and bacteria impermeable lightweight, flexible plastic liner to prohibit any passage of fluid or bacteria through said head cover; and a fluid absorbing inside layer that touches the wearer's skin; said head cover having excess absorbing material at the user's forehead area to form a fluid trap to hold excess fluid splash while the outer layer, absorbs the fluid splash, thereby preventing fluid from running down said member.

2. The apparatus as described in claim 1 further including:

vent means disposed at substantially the top of said head cover.

3. The apparatus as described in claim 2 wherein:

said head cover is dimensioned and configured to be larger than the largest normal user's head; and said head cover drapes over the top of the user's head; and includes draw bands.

4. The apparatus as described in claim 3 wherein:

said head cover includes a rubber band to maintain a snug fit.

5. A device for protecting the face including the eyes, nose, ears and mouth, which comprises:

a clear plastic member disposed generally in the form of a cylindrical section;

two spring loaded, rubber lined clips fixed on said member at spaced points and securing said member proximate to the edges thereof to associated temple frames of associated eyeglass frames;

said member having attached to the top and sides thereof a multiple layered head cover;

said head cover having a fluid absorbent outside layer for absorbing fluid spatter; a fluid and bacteria impermeable lightweight, flexible plastic liner to prohibit any passage of fluid or bacteria through said head cover; and a fluid absorbing inside layer that touches the wearer's skin; said head cover having excess absorbing material at the user's forehead area to form a fluid trap to hold excess fluid splash while the outer layer absorbs the fluid splash, thereby preventing fluid from running down said member.

6. The apparatus as described in claim 5 wherein:

said head cover is dimensioned and configured to be larger than the largest normal user's head; and said head cover drapes over the top of the user's head; and includes draw bands.

* * * * *